(12) United States Patent
McCarthy et al.

(10) Patent No.: US 6,479,818 B1
(45) Date of Patent: Nov. 12, 2002

(54) APPLICATION OF X-RAY OPTICS TO ENERGY DISPERSIVE SPECTROSCOPY

(75) Inventors: Jon J. McCarthy, Middleton, WI (US); David J. McMillan, Middleton, WI (US)

(73) Assignee: Thermo Noran Inc., Middleton, WI (US)

( * ) Notice: Subject to any disclaimer, the term of this patent is extended or adjusted under 35 U.S.C. 154(b) by 0 days.

(21) Appl. No.: 09/397,809

(22) Filed: Sep. 17, 1999

Related U.S. Application Data

(60) Provisional application No. 60/100,741, filed on Sep. 17, 1998.

(51) Int. Cl.⁷ .......................... H01J 37/26; H01J 37/244
(52) U.S. Cl. .......................... 250/310; 250/307; 250/397
(58) Field of Search ................................ 250/310, 307, 250/397

(56) References Cited

U.S. PATENT DOCUMENTS

| | | |
|---|---|---|
| 1,865,441 A | 7/1932 | Mutscheller |
| 2,819,404 A | 1/1958 | Herrnring et al. |
| 3,143,651 A | 8/1964 | Giacconi et al. |
| 3,920,999 A | 11/1975 | Drexler et al. |
| 3,963,922 A * | 6/1976 | Zulliger et al. ............. 250/310 |
| 4,242,588 A | 12/1980 | Silk et al. |
| 4,317,036 A | 2/1982 | Wang |
| 4,599,741 A | 7/1986 | Wittry |
| 4,785,470 A | 11/1988 | Wood et al. |
| 4,825,454 A | 4/1989 | Annis et al. |
| 4,916,721 A | 4/1990 | Carr et al. |
| 5,016,267 A | 5/1991 | Wilkins |
| 5,033,074 A | 7/1991 | Cotter et al. |
| 5,192,869 A | 3/1993 | Kumakhov |
| 5,263,075 A | 11/1993 | McGann et al. |

(List continued on next page.)

FOREIGN PATENT DOCUMENTS

| | | |
|---|---|---|
| WO | WO 97/14156 | 4/1997 |
| WO | WO 99/09401 | 2/1999 |

OTHER PUBLICATIONS

D. A. Carpenter & M. A. Taylor, Nondestructive Microanalysis with a Laboratory–Based X–Ray Microprobe, Microbeam Analysis 2 (suppl.), pp. S84–S85, 1993.

Brian R. York, Fabrication and Development of Tapered Capillary X–Ray Optics for Microbeam Analysis, Microbeam Analysis, Microbeam Analysis 4 (suppl.), pp. 153–154, 1995.

D. X. Balaic, et al., X–ray Optics of Tapered Capillaries: Theory and Experiment, Microbeam Analysis 4 (suppl.), pp. 155–156, 1995.

Qi–Fan Xiao & Ning Gao, Tapered Multicapillary Optics for X–Ray Focusing, Microbeam Analysis 4 (supp.), pp. 157–158, 1995.

(List continued on next page.)

*Primary Examiner*—Bruce Anderson
(74) *Attorney, Agent, or Firm*—Foley & Lardner

(57) ABSTRACT

An x-ray optic is employed in combination with an energy dispersive spectroscopy (EDS) detector to enhance detection performance. Such a combined optic and detector may be employed in scanning electron microscope or environmental scanning electron microscope (ESEM) applications. The x-ray optic may be a grazing incidence optic (GIO) employed as a flux enhancing collimator for use with an EDS detector, used to perform electron beam microanalysis. It is found that the GIO in combination with an EDS provides substantial intensity gain for x-ray lines with energy below 1 keV. The GIO is also found to provide a modest focus effect, i.e., by limiting the field of view of the detector, and introduces minimal spectral effects. The combined optic and detector is useful in applications employing broad beam excitation, such as an ESEM or a system using x-ray fluorescence, to spatially limit the x-rays of interest to those within the acceptance angle of the optic.

11 Claims, 8 Drawing Sheets

U.S. PATENT DOCUMENTS

| | | |
|---|---|---|
| 5,265,143 A | 11/1993 | Early et al. |
| 5,265,144 A | 11/1993 | Harding et al. |
| 5,268,951 A | 12/1993 | Flamholz et al. |
| 5,274,435 A | 12/1993 | Hettrick |
| 5,333,166 A | 7/1994 | Seligson et al. |
| 5,362,964 A * | 11/1994 | Knowles et al. ............ 250/310 |
| 5,384,817 A | 1/1995 | Crowther et al. |
| 5,394,451 A | 2/1995 | Miyake et al. |
| 5,408,512 A | 4/1995 | Kuwabara et al. |
| 5,481,109 A | 1/1996 | Ninomiya et al. |
| 5,497,008 A | 3/1996 | Kumakhov ............... 250/505.1 |
| 5,570,408 A | 10/1996 | Gibson |
| 5,682,415 A | 10/1997 | O'Hara ....................... 378/147 |
| 5,745,547 A | 4/1998 | Xio |
| 5,747,821 A | 5/1998 | York et al. |
| 5,812,631 A | 9/1998 | Yan et al. |
| 5,903,004 A | 5/1999 | Koshihara et al. .......... 250/310 |
| 5,926,522 A | 7/1999 | McCarthy et al. |

OTHER PUBLICATIONS

N. Gao, et al., Monolithic polycapillary focusing optics and their applications in microbeam x-ray fluroescense, Appl. Phys. Lett. 69 (11), pp. 1529–1531, 1996.

R. Agnello, et al., The Use of Collimating X–Ray Optics for Wavelength Dispersive Spectroscopy, Microsc. Microanal. 3(2), pp. 889–890, 1997.

J.P. Kirkland, et al., Wavelength–dispersive x–ray fluorescence detector, Rev. Sci. Instrum., 66(2), pp. 1410–1412, Feb., 1995.

* cited by examiner

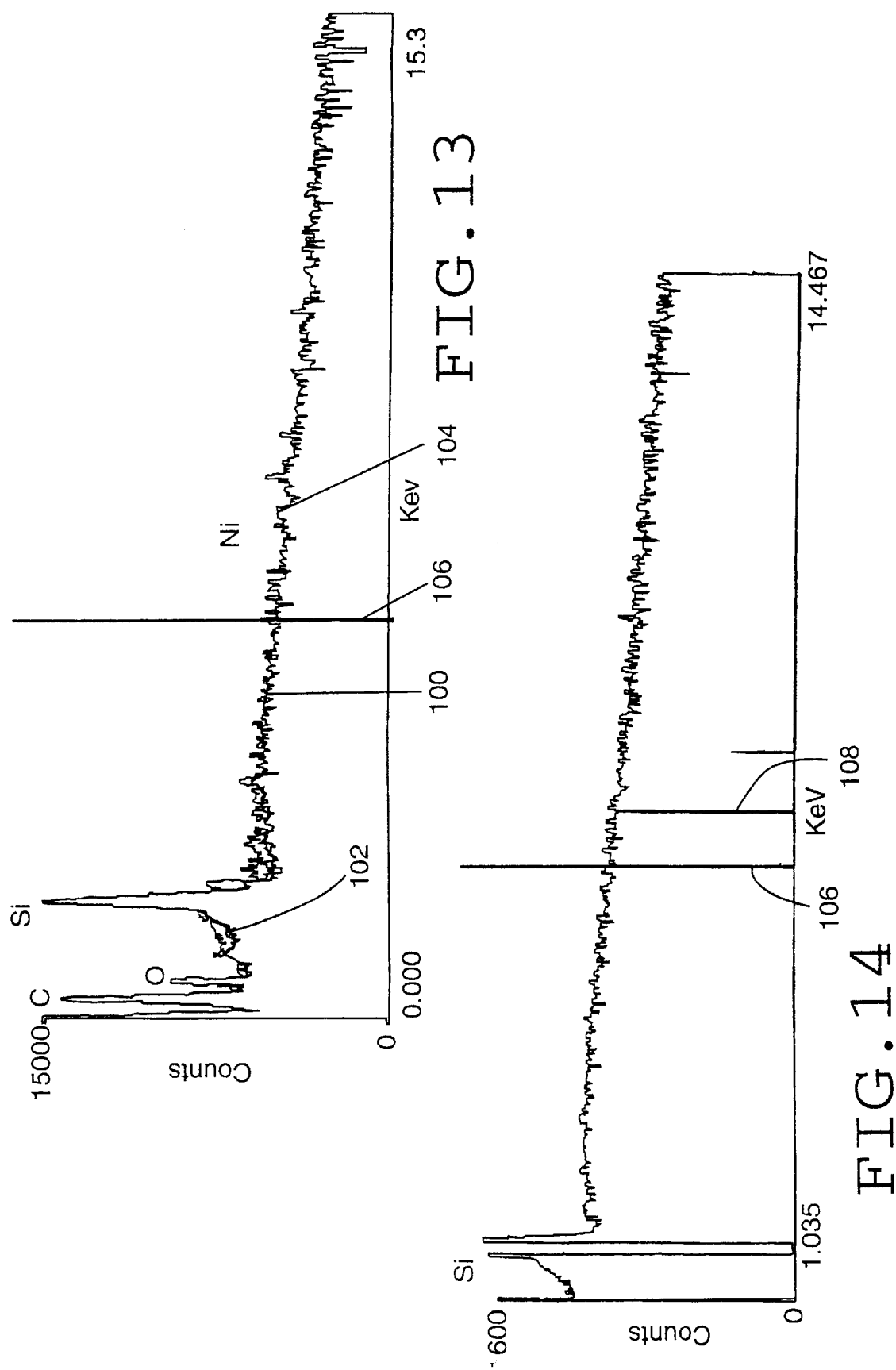

APPLICATION OF X-RAY OPTICS TO ENERGY DISPERSIVE SPECTROSCOPY

This application claims the benefit of U.S. Provisional Application No. 60/100,741, filed Sep. 17, 1998.

FIELD OF THE INVENTION

This invention pertains generally to the field of x-ray spectroscopy and particularly to x-ray optics for spectroscopy.

BACKGROUND OF THE INVENTION

The electron beam striking a sample in an electron microscope produces x-rays that are characteristic of the material of the sample that is impacted by the electron beam. Consequently, x-ray spectroscopes have been mounted to electron microscopes to analyze the x-rays emanating from the sample. X-rays at wavelengths characteristic of the sample are also produced by fluorescence from interaction of an x-ray beam with the sample, such as in x-ray microscopes. In energy dispersive spectroscopy (EDS), a solid state detector is positioned relatively close to the sample to collect x-rays emanating from the sample. The EDS detector receives and must detect x-rays of many wavelengths, and the resolution of the EDS system is limited by the resolution capability of the available solid state detectors.

In wavelength dispersive spectroscopy (WDS), the x-rays emanating from the sample are reflected from a wavelength dispersive element, typically a crystal or multi-layer diffracting element, which reflects the various wavelengths at specific angles. By changing the orientation of the diffracting element or of the position of the detector or both, the wavelength of x-rays that are incident upon the detector after redirection by the diffracting element can be selected, allowing relatively high precision spectroscopy with a capability of resolving relatively narrow peaks.

X-ray optics are employed in x-ray analytical instruments for focusing x-rays into high intensity spots, or for collimating x-ray beams. Exemplary applications for x-ray optics include microfluorescence, microdiffraction, tomography and lithography, and WDS. It has been pointed out that the use of an x-ray optic in a collimating configuration could provide enhanced detection sensitivity in WDS. WDS devices have been specifically designed to use grazing incidence collimating x-ray optics.

A few studies have appeared reporting the use of x-ray optics in applications using EDS. Focusing x-ray optics have been used on both the excitation and detection side of EDS systems. An x-ray microprobe which employs a monocapillary optic has been described. Polycapillary optics have been used to provide an intense convergent beam of x-rays from a microfocus x-ray tube to excite a sample for x-ray microfluorescence studies. A polycapillary optic has been used to increase the effective area of a microcalorimeter EDS. An intensity gain of nearly 300 (ratio of peak intensity with and without optic in place) with a fixed detector to sample distance of 66 mm was reported.

SUMMARY OF THE INVENTION

In accordance with the present invention, an x-ray optic is combined with an energy dispersive spectroscopy (EDS) detector to enhance the performance thereof. The x-ray optic may be a grazing incidence-type optic, a glass polycapillary-type x-ray optic, a hybrid grazing incidence/polycapillary-type optic, or any other known x-ray optic which may be employed in combination with an EDS detector in accordance with the present invention. Such an x-ray optic is employed to narrow the field of view of the EDS detector. This function of the x-ray optic is particularly applicable to improve EDS detection in broad beam spectroscopy applications, such as those employing environmental scanning electron microscopes (ESEM) and x-ray fluorescence.

In accordance with a preferred embodiment of the present invention, a compact grazing incidence x-ray optic is combined with a standard semi-conductor EDS detector. A grazing incidence optic (GIO) may be employed as a flux enhancing collimator for use with an EDS detector used to perform electron beam microanalysis. A GIO in combination with an EDS detector in accordance with the present invention provides substantial intensity gain for x-ray lines with energy below 1 keV. The GIO also provides a modest focusing effect, i.e., by limiting the field of view of the EDS detector, and introduces minimal spectral artifacts.

In accordance with the present invention, an x-ray optic employed in combination with an EDS detector may be employed as part of a conventional scanning electron microscope (SEM) or in broad beam spectroscopy applications such as in an ESEM, in which a specimen is analyzed in a relatively high ambient pressure, contrasted to normal SEMs operating under high vacuum, or spectroscopy employing x-ray fluorescence.

Further objects, features, and advantages of the invention will be apparent from the following detailed description when taken in conjunction with the accompanying drawings.

BRIEF DESCRIPTION OF THE DRAWINGS

FIG. 13 is a comparison of two SiC spectra which illustrates the presence of an artifact caused by use of a GIO in combination with an EDS detector.

FIG. 14 is a comparison of $SiO_2$ spectra collected using a GIO optic in combination with an EDS detector in accordance with the present invention with and without carbon paint applied to the tip of an outside surface of the GIO to reduce artifacts.

DETAILED DESCRIPTION OF THE INVENTION

Figure 1:
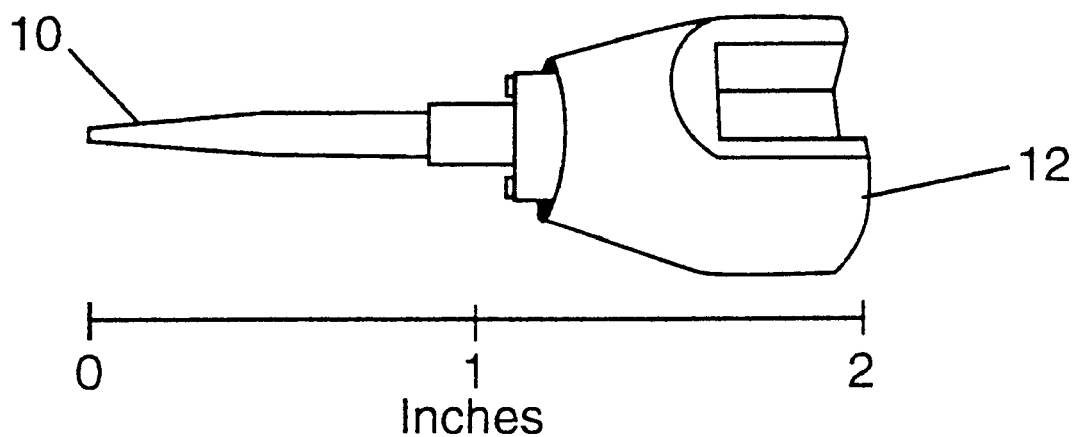
FIG. 1 is an illustration of an exemplary x-ray optic collimator assembly for use with an energy dispersive spectroscopy (EDS) detector in accordance with the present invention.

In accordance with the present invention, an x-ray optic is employed in combination with a conventional energy dispersive spectroscopy (EDS) detector to improve EDS detection performance. The present invention will be described in detail with reference to the exemplary embodiment of a grazing incidence x-ray optic in combination with an EDS detector, as used in a scanning electron microscope (SEM). It should be understood, however, that other x-ray optics, such as polycapillary and hybrid polycapillary/grazing incidence x-ray optics, may also be employed, and that such a combination may be employed in other electron microscope devices, such as an environmental SEM.

Replicated grazing incidence x-ray optics (GIO) have the benefits of being compact in size, relatively inexpensive, and highly efficient reflectors for x-ray energies below 1 keV. GIOs utilize the principle of total external reflection for the efficient collection of x-rays. These optics reflect x-rays only for very small angles of incidence with respect to the reflecting surface, and the reflectivity is a strong function of grazing angle and x-ray energy. Hence, the shape of a particular optic must be optimized for the specific application in mind. Normally, GIOs are composed of figures of revolution comprising sections such as cones, parabolas, hyperbolas, or ellipsoids. More complex figures, which combine a plurality of any one shape or combination of more than one shape, or even several separate reflectors, may also be employed. The reflecting surfaces may consist of a thin, very smooth layer of material, commonly a metal or metal alloy. Since the reflectivity is a strong function of the material of the reflecting surface, care must be taken to match the material to the needs of a particular application. Micro-roughness of the reflecting surface can cause scattering in unwanted directions and reduce the efficiency of the optic. Hence, the shape of the reflecting surface and its smoothness must be carefully controlled to obtain the best performance. Since a GIO is at least a semi-focusing device, it may be employed to limit the field of view of an x-ray detector. In practice, this effect will be strongly dependent on various other design considerations, including the x-ray energy range of interest, the desired flux gain, the working distance between the sample and the optic, and the size of the x-ray detector.

In accordance with the present invention, a GIO is not required to collimate or focus the x-rays emerging from a sample, but only to redirect them through an aperture of a specified size. This aperture is the surface of the EDS detector. Because the x-ray flux merely has to pass through the aperture, and not form a parallel beam, the optic is best described as a flux concentrator, not a collimator. However, throughout this description, we will refer to the assembly which contains the optic as the "optic collimator", in keeping with the convention that a device mounted on the end of an EDS detector which limits the field of view of the detector chip is referred to as a collimator.

An exemplary x-ray optic for use in combination with an EDS detector in accordance with the present invention is illustrated in FIG. 1. In this exemplary embodiment, the x-ray optic 10 is a GIO. The GIO 10 is mounted via a mounting assembly 12 onto the EDS detector. The shape and size of the GIO 10 and mounting assembly 12 shown in FIG. 1 are for a 10 $mm^2$ EDS detector.

Figure 2:
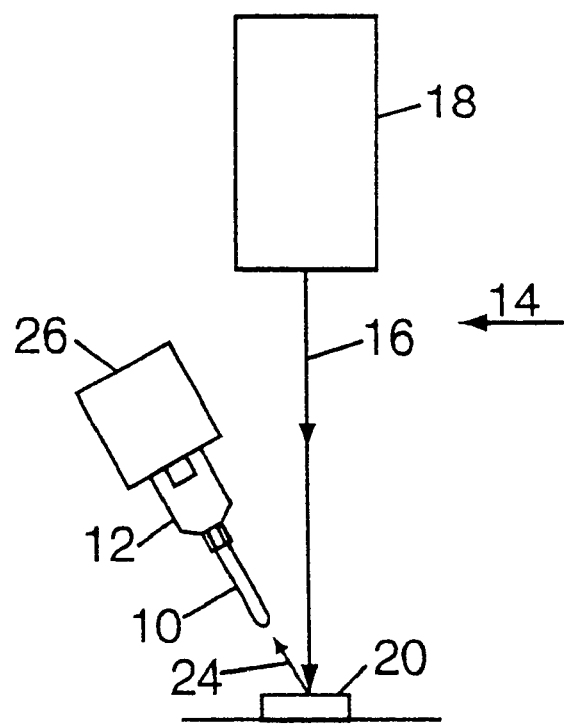
FIG. 2 is a schematic illustration of an x-ray optic in combination with an EDS detector in accordance with the present invention as employed in a scanning electron microscope (SEM).

Tests were performed to verify the enhanced performance of a combined x-ray optic and EDS detector in accordance with the present invention. The tests were performed using SEMs. As illustrated in FIG. 2, in an SEM 14, an electron beam 16 generated by an electron source 18 is directed onto a sample 20. As a result of the impact of the electron beam 16 with the sample 20, x-rays 24 are emitted from the point of impact on the sample 20. The energies of the x-rays 24 emitted from the sample 20 are indicative of the chemical constituents of the sample 20 at the point of impact of the electron beam 16. A portion of the x-rays 24 emitted from the sample 20 pass into the x-ray optic 10, which is attached to an EDS detector 26, via the mounting assembly 12. As discussed previously, the x-ray optic 10, which may be a GIO, redirects the x-rays entering the optic onto a detector surface in the EDS detector 26. (Note that FIG. 2 is a schematic illustration, the angles and distances between objects shown in FIG. 2 are not drawn to scale.)

Tests were performed on several microscopes, in horizontal and inclined geometries, and at various accelerating voltages (25, 20, 15, 10, and 5 kV). Since results at different voltages were very similar, results for only one accelerating voltage will typically be reported herein. Measurements were performed with the GIO x-ray optic on horizontal entry 10 $mm^2$ and 30 $mm^2$ Si(Li) EDS detectors with Hitachi S-520 and S-650 SEMs and with a 10 $mm^2$ Si(Li) detector at a 40° incline in a JEOL JSM-840 SEM. The sample was tilted to 30° for the horizontal entry measurements, and was flat for the measurements in the inclined entry geometry. The sample to detector position was varied, but the minimum distance was about 50 mm in all cases.

Each optic 10 was combined with a mounting assembly 12 to form a collimator that could be fitted onto a standard Si(Li) detector in place of the normal collimator. The grazing incidence optics were designed to have an optimum focus position 4 mm from the sample. At the 4 mm position, the detector crystal was 50 mm from the sample. In all cases, the optic was rigidly aligned with the detector, since the optic position relative to the Si(Li) crystal is not critical. The rigid mount allows the normal alignment adjustments on the EDS to be used to align the optic in the x-ray plane of the specimen. Alignment of the optic on the microscope was carried out by adjusting the sample working distance and the EDS X-Y adjustments until the count rate reached a maximum. Once the optimum working distance was found, it was not changed when measurements were made without the optic in place.

With the optic collimator in place, a series of measurements were carried out in order to characterize the performance of the GIO. The GIO was evaluated in both horizontal entry and inclined entry geometries, at various x-ray energies, and with multi-element samples. Each optic was tested to determine (1) the gain of the optic relative to the EDS at the same position without the optic, (2) the reproducibility of x-ray intensity with repeated repositioning of the EDS;

(3) the variation in intensity across the focal spot of the optic; and (4) the presence of any artifacts in the x-ray spectrum.

Optic Gain

The gain of each optic was measured as a function of energy, and for the grazing incidence optic, as a function of optic position. The gain of the optic is defined as the ratio of the x-ray intensity measured with the optic collimator in place, to the x-ray intensity measured without the optic collimator in place, but with the detector in the same position. All excitation conditions were kept constant when measured (beam current) during the test. The intensity of various peaks in the spectrum was measured as the net counts extracted by a filtered least squares fit of the spectrum normalized to counting time and beam current. By repeating the measurements for a series of pure element or a few multi-element standards, the gain at the characteristic energies of multiple elements was measured, and hence the gain of the optic as a function of x-ray energy was deduced.

Figure 3:
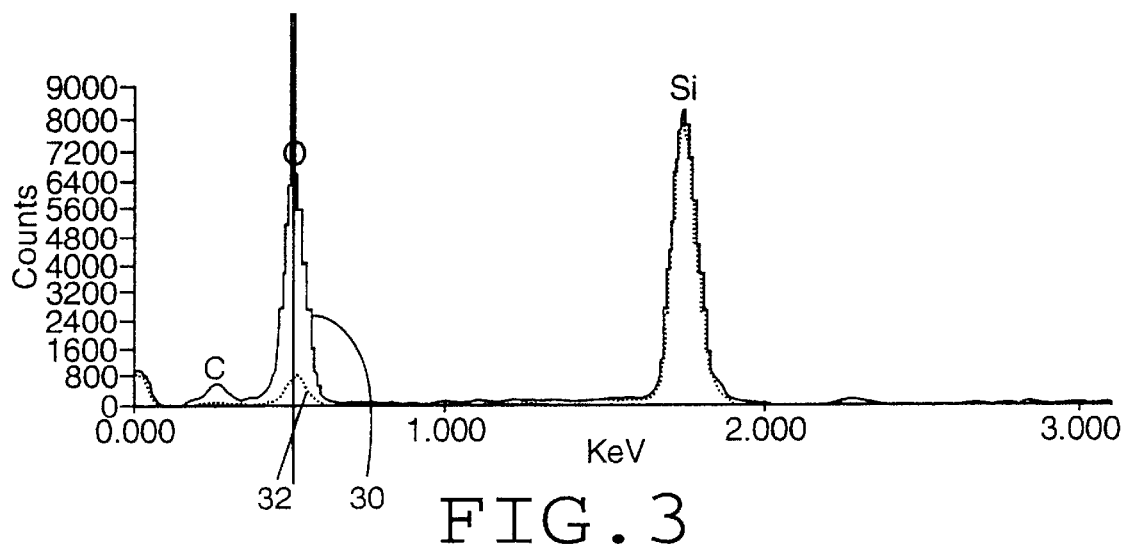
FIG. 3 is an illustration of an $SiO_2$ spectrum obtained using an EDS detector with and without a grazing incidence optic (GIO) in place.
Figure 4:
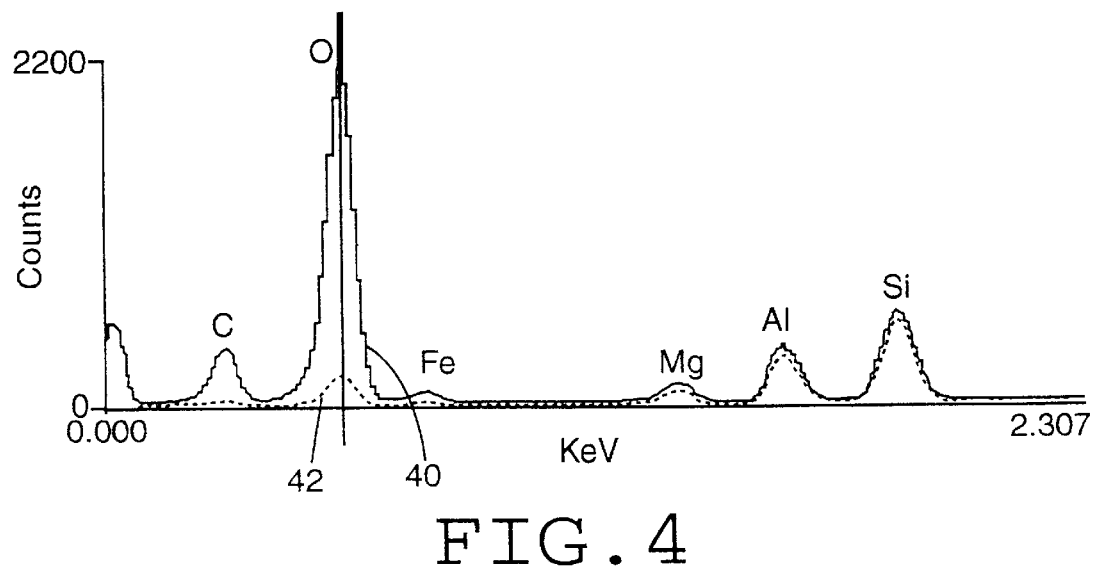
FIG. 4 is an illustration of a Pyrope Garnet mineral spectrum obtained using an EDS detector with and without a GIO in place.
Figure 5:
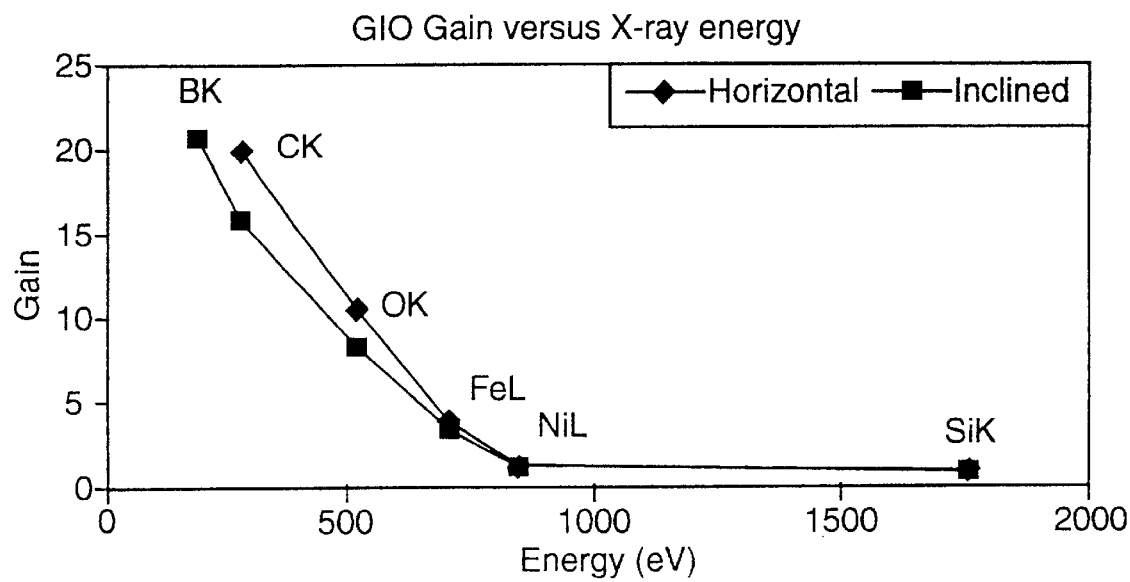
FIG. 5 is a chart of the measured gain of GIO collimators as a function of x-ray energy.

FIG. 3 is an illustration of a comparison of the spectra obtained from a sample of $SiO_2$ with 30 and without 32 the GIO in place. It is readily apparent that the oxygen and carbon peaks have been enhanced by the GIO, while the silicon shows little or no enhancement. A similar result for a multi-element mineral is shown in FIG. 4, which illustrates the comparison of a Pyrope Garnet mineral spectrum obtained with 40 and without 42 the GIO in place. After processing the spectra from a series of measurements in both horizontal and inclined geometries, a plot of intensity gain versus x-ray energy for the GIO was obtained. The result is shown in FIG. 5. The gain for boron was only measured in the inclined geometry, and is a factor of about 22. The gain for carbon is a factor of 20 in the horizontal geometry and 16 in the inclined geometry. It is believed that the difference is due to the difference in absorption of the emitted x-rays due to the difference of path length leaving the sample in each case. The gain declines until about 1 keV, after which there is little or no gain.

Figure 6:
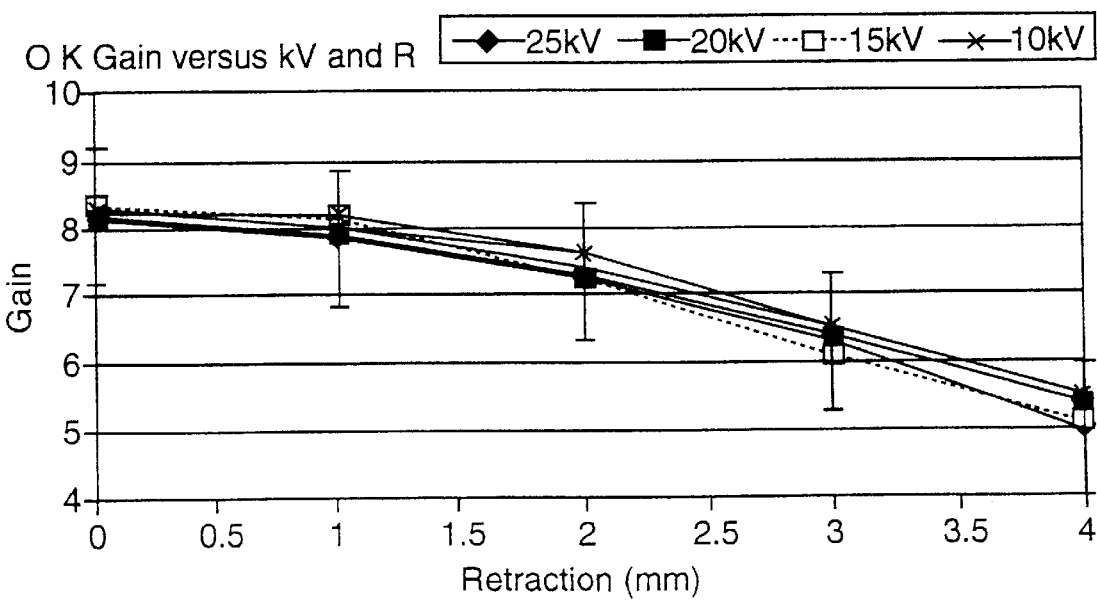
FIG. 6 is a graph of the GIO gain for oxygen as a function of electron beam Kv and retraction of the EDS detector from the optimum focus position for the GIO.
Figure 7:
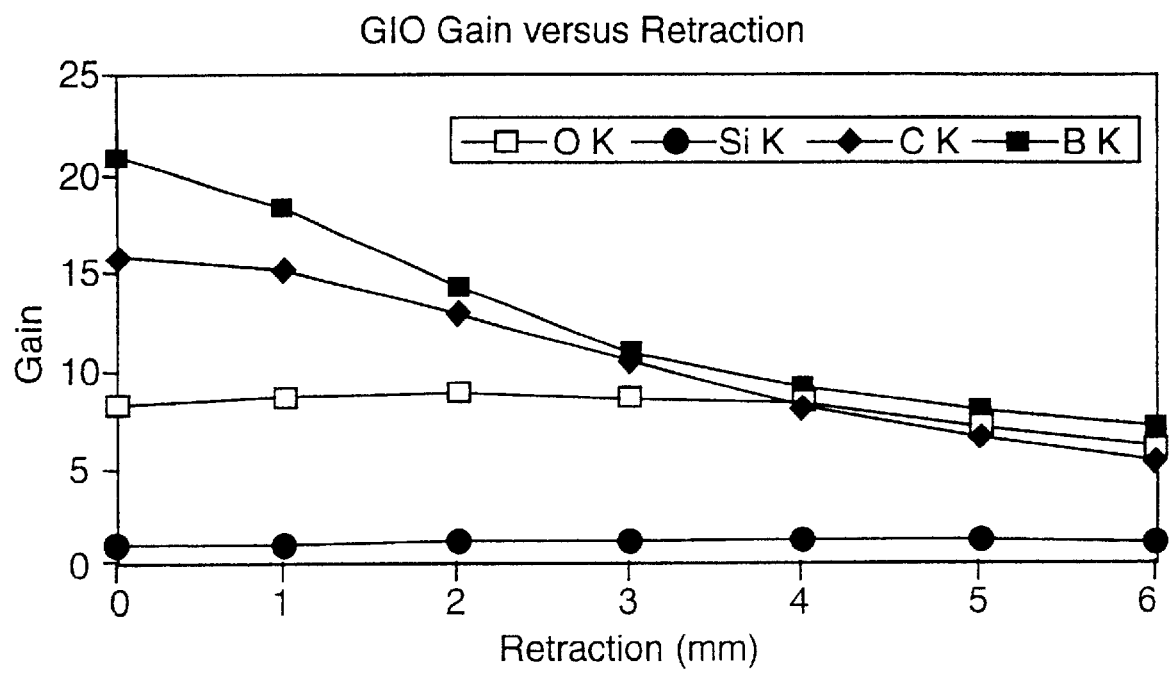
FIG. 7 is a graph of the variation of the measured gain for an inclined geometry GIO as a function of retraction.

The effect on the elements that exhibit optic gain of changing the kV and retraction of the combined GIO/EDS from the optimum focus position was also investigated. The results of these measurements are given in FIGS. 6 and 7. In FIG. 6, the gain for oxygen in the inclined geometry as a function of kV is plotted against the amount of retraction from the 4 mm position (shown as a retraction of 0 mm). Statistical error bars have been shown on the 25 kV data only, but the errors on each trace are approximately equal. This implies that at each retraction the measured gains are all statistically the same and that kV has little or no effect on the gain. The same lack of dependence on kV result was obtained for other elements. The variation of the oxygen gain as a function of retraction was smoothly varying, and declines by about 40% over a 4 mm distance. The oxygen data is repeated in FIG. 7 for comparison to the behavior of the measured gain for several other elements. The gain for lighter elements declines more rapidly at first than does the gain for heavier elements. Indeed, for silicon, there is little effect at all, since at this energy, the GIO functions more like a simple geometric collimator with no gain at all.

Figure 8:
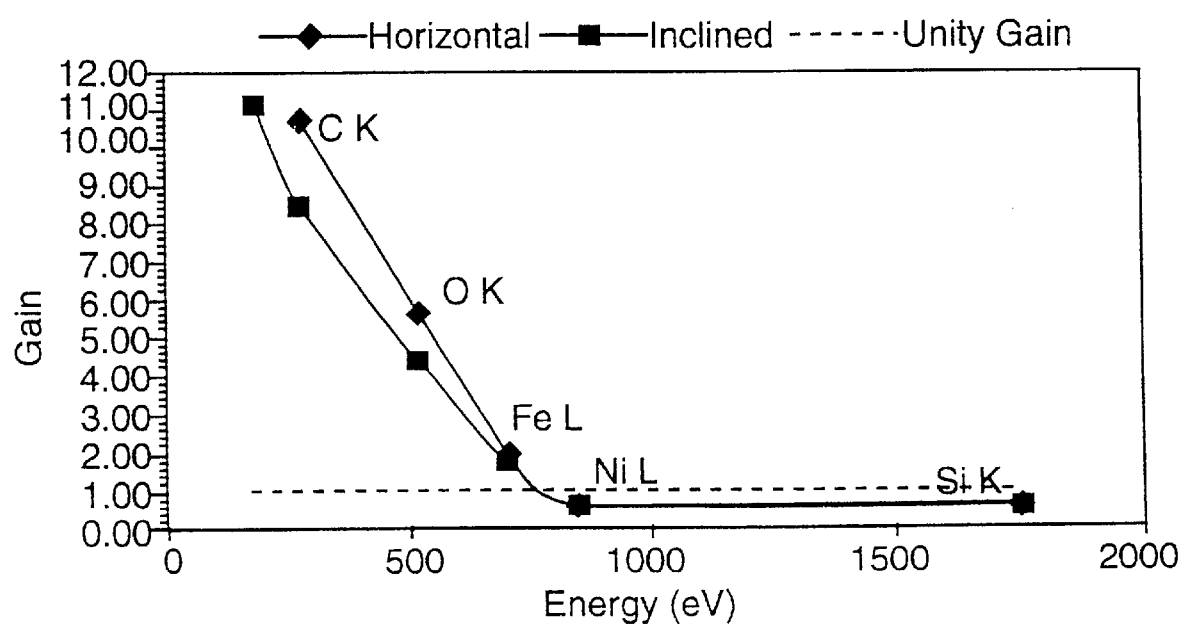
FIG. 8 is a graph of the gain of an EDS detector without an x-ray optic but positioned closer to a sample.

Although the gains measured for x-rays below about 1 keV are rather dramatic, it is important to consider how the detector with the GIO compares to a detector of the same cross-sectional area which could be placed closer to the sample without a GIO. A database of over 450 current detector designs was reviewed and the average minimum detector to sample distance with a standard collimator was calculated. With a standard collimator and an electron trap mounted, the average minimum detector to sample distance is 36.5 mm. At this position, the detector collects about 1.9 times the intensity it does at 50 mm. The data of FIG. 5 has been replotted in FIG. 8 to show the gain compared to a detector without an optic at 36.5 mm. The gains for the lighter elements are still quite good. However, for x-ray energies above 1 keV, there is a reduction in intensity to about 57% of that with the GIO in place and a detector positioned at 50 mm.

Position Reproducibility Testing

Position reproducibility testing was carried out by retracting the entire EDS detector and collimator assembly, then repositioning it to the optimum optic focus position as indicated by the scale on the detector mount. The inward travel of the detector motion was limited by a physical stop on the mechanism, which was set initially and not changed during the test. After each repositioning, a 300 second spectrum was collected, and the intensity of various peaks in the spectrum was measured as the net counts extracted by a filtered least squares fit of the spectrum normalized to counting time and beam current. The data from a set of repeated trials were plotted and tested to see if they were constant within the statistics of the measurement. All excitation conditions were kept constant or measured (beam current) during the test.

Figure 9:
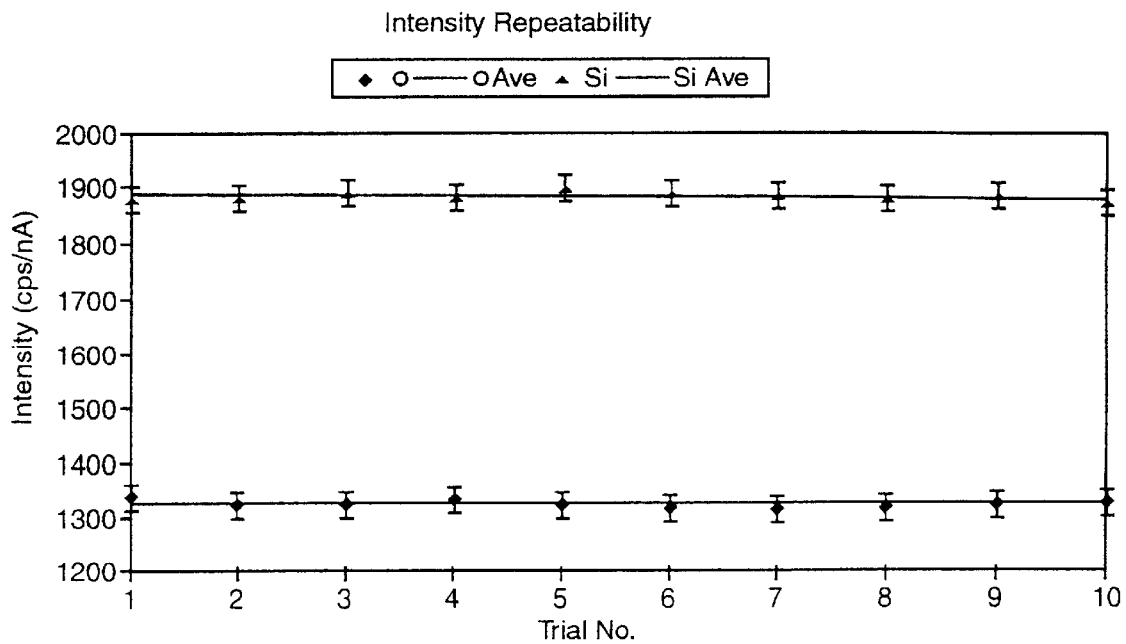
FIG. 9 is a chart illustrating repeatability of detected peak intensities with a combined GIO and EDS detector for oxygen and silicon.

The tests were carried out with a variety of samples containing various elements, in order to test for any dependence on x-ray energy. The results for oxygen and silicon from a $SiO_2$ sample are shown in FIG. 9. The horizontal axis is the number of each trial in which the detector was retracted and then reinserted to a mechanical stop before the spectrum was recorded and the intensity calculated. Each point represents a single intensity measurement and is shown with the statistical error calculated in the intensity extraction process. The error bars represent +/- three sigma values. The solid lines represent the average value of the intensity for each element obtained from all ten trials.

In all cases for which measurements were made, when using the mechanical stop, the intensities were constant within the statistical variation of the measurements. When reinsertion was performed without the stop, by relying on the pointer on the detector slide and the human eye alone, the variation for low energy x-rays would often exceed the measured statistical variation. Such a result is not unexpected on the basis of FIG. 7. The position error without the stop was estimated to be 0.1 to 0.3 mm. Since the gain for low energy x-rays drops fairly sharply as a function of retraction, the decrease in gain can easily exceed the variance in the intensity measurement. This increased sensitivity to the mechanical precision in positioning the EDS may be one of the penalties of using a GIO, and perhaps any x-ray optic, with an EDS.

Intensity Variation with Beam Position

After the optic was aligned, as determined by maximizing the input count rate, tests were conducted to measure the response of the collimator optic to variations in the position of the beam with the position of the sample. With the SEM in spot mode, x-ray spectra were collected as the beam was placed at different positions across the input focal spot of the optic. At each position, the intensity of various peaks in the spectrum was measured as the net counts as obtained by the method described above. In several cases, variation due to sample motion in the Z direction was also measured as the sample was moved up and down. These tests map the region of the sample which was seen by the optic collimator (the "field of view"), and therefore of the EDS system.

A series of measurements were made to investigate the focusing properties of the GIO. After the GIO had been aligned for maximum intensity, the sensitivity to changes in working distance of the sample (Z focus) and X or Y beam position (lateral focus) was tested. At low magnification, the end of the optic could be observed in the SEM image. The optic was centered in the field of view, and a millimeter scale drawn on the SEM CRT, roughly centered on the center of the optic. The beam was then placed in spot mode and (after accounting for any scan shift) placed at the center of the scale. For Z focus data, the beam was left in this position, and the sample moved up and down with the stage Z access control. The upward motion of the sample was always limited to a few millimeters, to avoid hitting the GIO with the sample. For the lateral focus data, the sample was left in the optimum Z position and the beam spot was moved horizontally across the optic field of view, along the scale on the CRT. X-ray intensity measurements were taken at each point.

Figure 10:
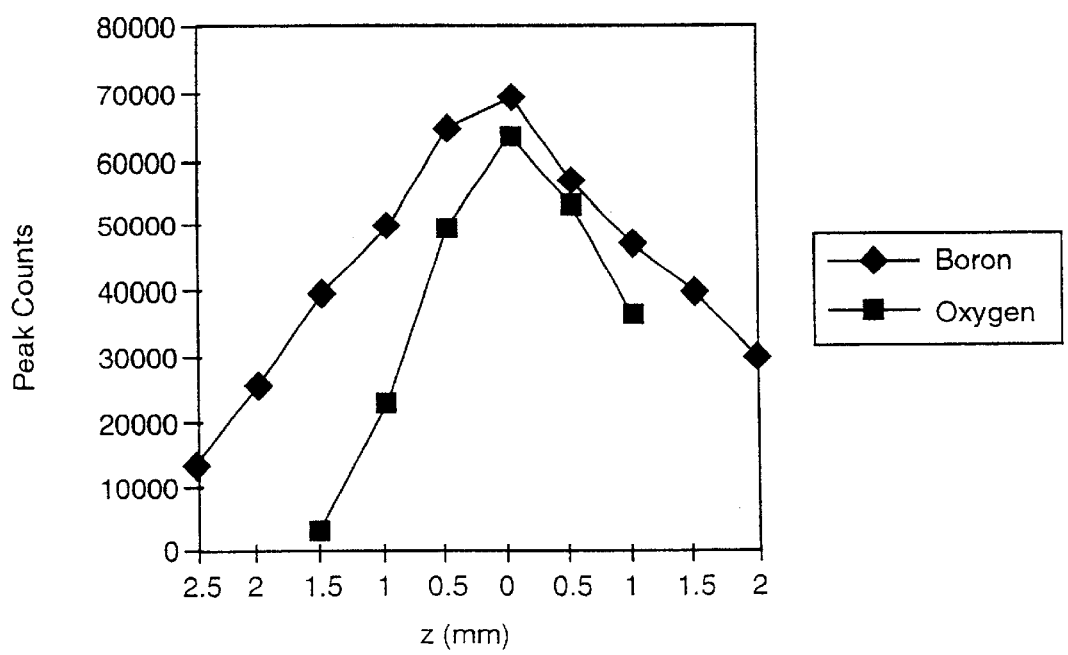
FIG. 10 is a graph of Z focus data for several elements using a GIO in combination with an EDS detector in accordance with the present invention.

The result of the Z focus data is shown on FIG. 10. Z focus data was only collected in the inclined geometry. The horizontal scale is distanced in mm above (−) or below (+) the optimum focus (highest intensity) point. The intensity plot shows a broad dependence on sample position, with a peaking behavior at the optimal position. The half maximum points on this curve occur at about +/−1.5 mm. The intensity seems to decline more slowly as the sample is moved down (away) from the optic.

Figure 11:
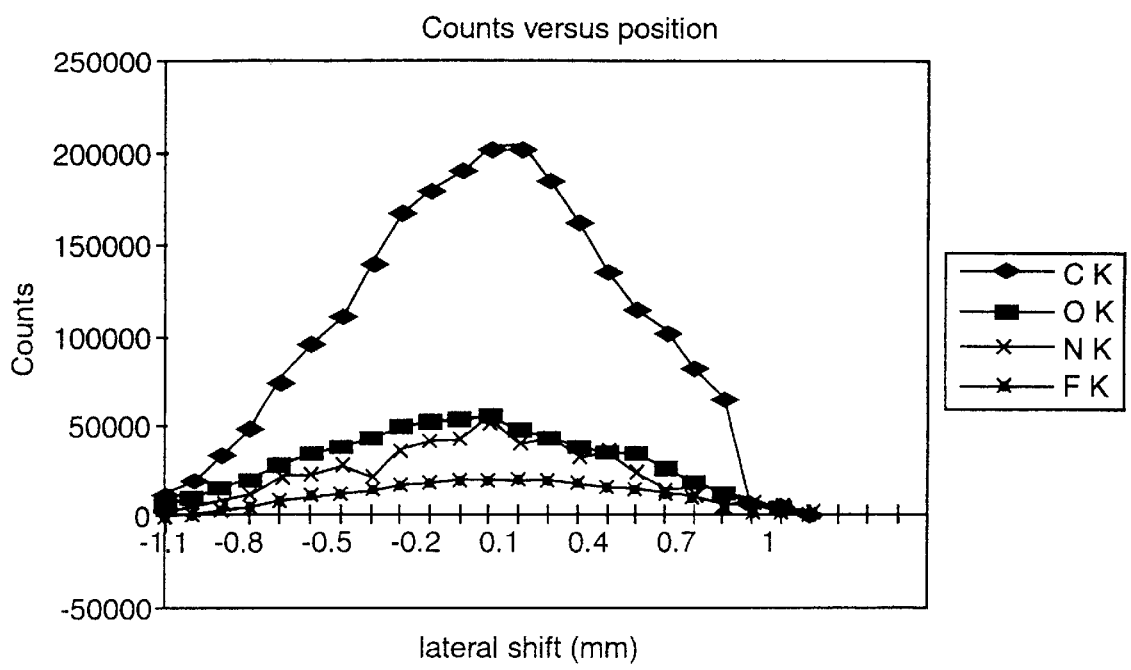
FIG. 11 is a graph of net peak counts as a function of SEM beam position for various elements with x-ray line energies below 1 keV, obtained using a GIO in combination with an EDS detector in accordance with the present invention.
Figure 12:
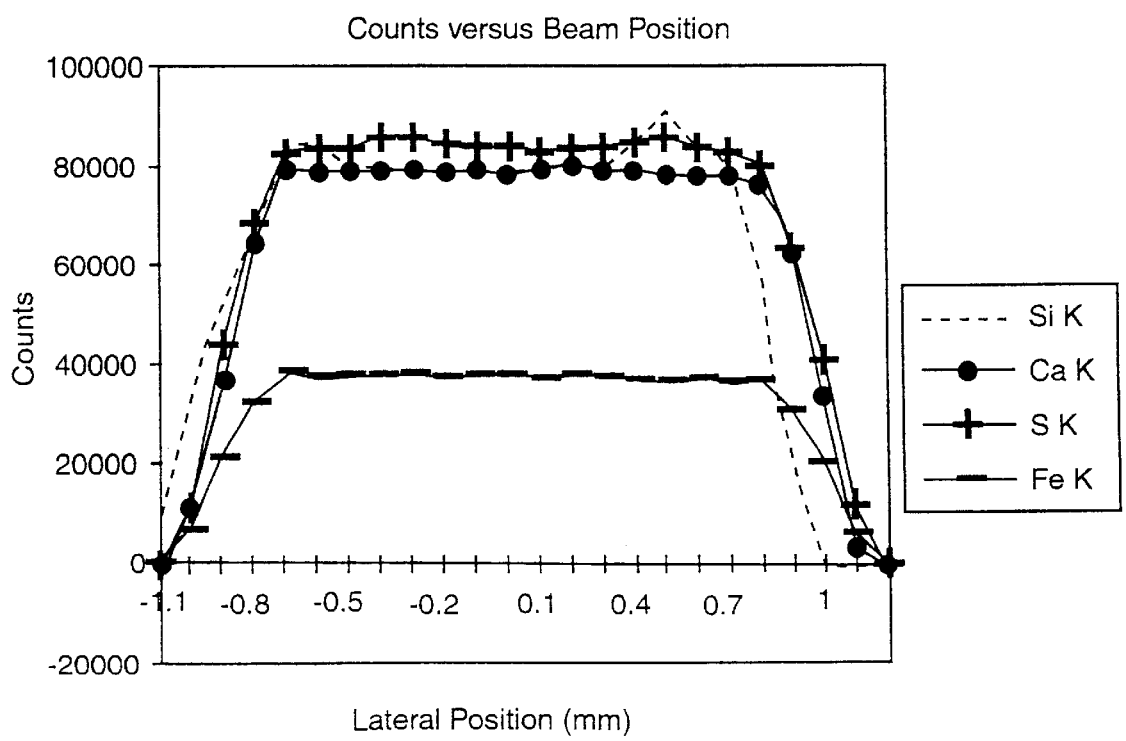
FIG. 12 is a graph of net peak counts as a function of SEM beam position for various elements with x-ray line energies above 1 keV, obtained using a GIO in combination with an EDS detector in accordance with the present invention.

The results of the lateral focus experiments are shown in FIGS. 11 and 12. In both figures, the horizontal axis gives the shift in mm from the center of the scale of the SEM CRT, which should be close to the center axis of the GIO. The vertical scale is the intensity of each x-ray line. By comparing the difference in the shape of the curves in these two figures, it can be seen that the behavior of the measured intensities is clearly separated on the basis of x-ray energy. In FIG. 11, x-ray lines with energies below 1 keV are plotted, and show a definite peak about the center point. The curves all have the same half maximum points, at about +/−0.6 mm. The width of the end of the optic is 2 mm. All exhibit intensity gain from the GIO and hence exhibit the peaking behavior. For x-ray lines with energies above 1 keV, the story is quite different, as is shown in FIG. 12. In this case, the curves sharply rise to a broad flat top before rapidly declining again. As before, the curves appear centered, but the half maximum points have moved out to about +/−0.9 mm. It is believed that, for these higher energy lines, there is no gain by reflection, and the GIO functions much like an ordinary mechanical collimator to limit the field of view of the EDS detector.

Spectral Artifacts Testing

Spectral artifacts were determined by a close inspection of spectra from various pure element and compound standards at multiple accelerating voltages. A combination of automatic and manual peak identification techniques were employed, as was direct comparison of spectra from the same sample obtained under identical excitation conditions with and without the optic collimator in place.

A spectrum 100 of SiC obtained with the GIO collimator in place is shown in FIG. 13. This spectrum 100 is overlaid with one 102 taken with the detector retracted 6 mm from the optimum focal position. The spectra has been normalized at the Si peak, since the gain at this point is unity. The vertical scale is logarithmic to emphasize small peaks at higher energy. The comparison shows that at the optimum focus position 100 (upper trace) a small peak 104 is present that is absent from the spectrum 102 obtained with the GIO retracted an additional 6 mm. The peak is identified as the NiK$\alpha$ line. Since the outer shell of the GIO, in this case, is made of nickel, the presence of this peak is not totally unexpected. Since there is no evidence of a corresponding NiL$\alpha$ line (at the marker 106), it is concluded that the NiK$\alpha$ peak is due to back scattered electrons striking the side of the GIO, and the L line is subsequently absorbed by the material of the optic. When the primary beam energy drops below about 10 kV, the NiK$\alpha$ artifact peak is no longer present. The Ni peak could also be eliminated by the application of carbon paint to the tip of the GIO. FIG. 14 shows a trace of SiO$_2$ spectra collected in one 300 second acquisition, after carbon paint was applied to the tip and outside surface of the GIO. Note that the Ni peak (marker 108) is absent, but a reduction in gain was noted, perhaps due to the lack of care in application of the carbon.

Figure 15:
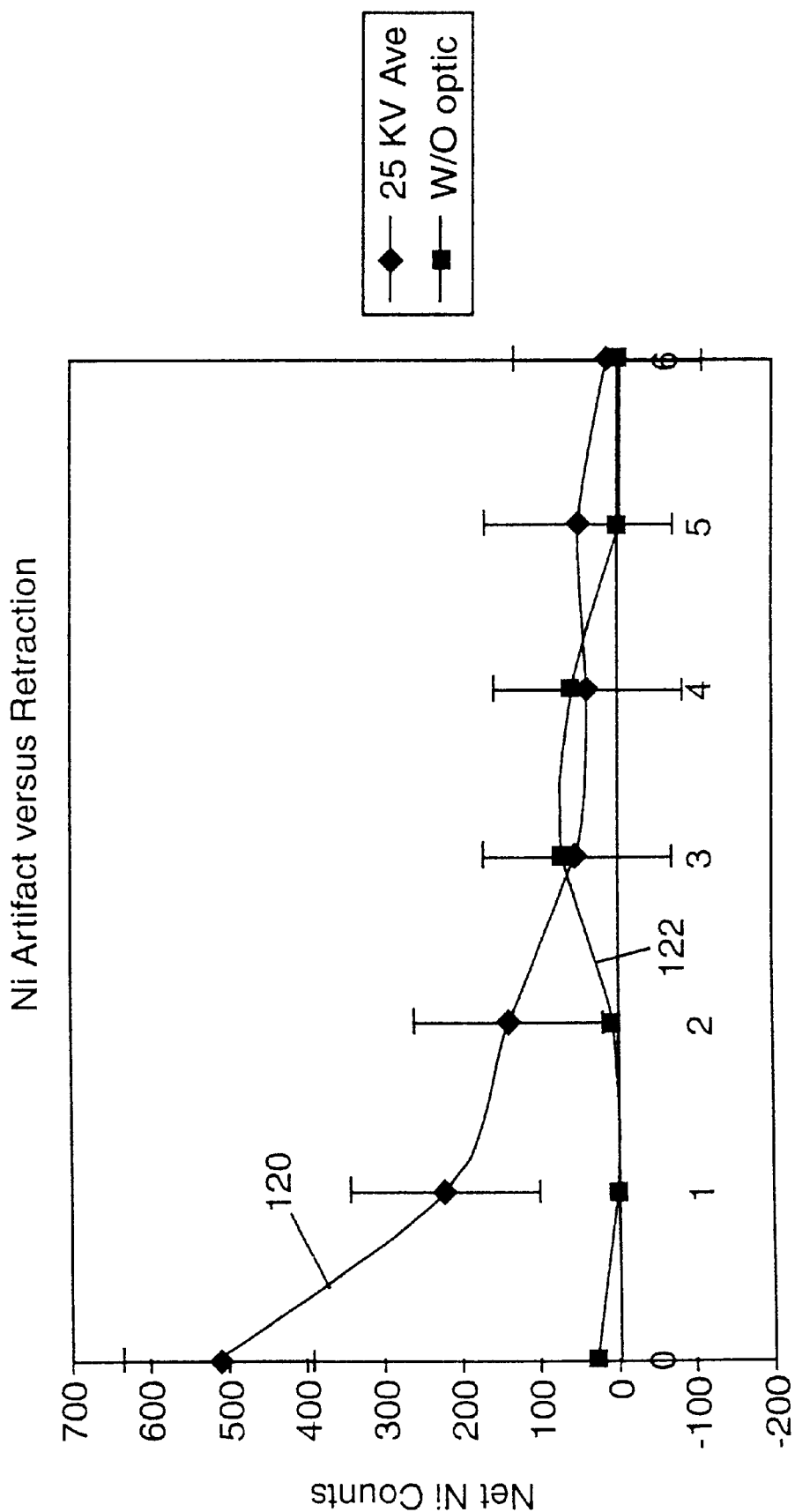
FIG. 15 is a graph of counts in an artifact peak as a function of retraction of the EDS and optic collimator.

The behavior of the Ni artifact as a function of the GIO position was also investigated. The EDS detector with GIO was retracted in 1 mm steps and the Ni counts measured at each point. Data was taken at a series of excitation voltages over the same range of retraction distances. The typical result is shown in FIG. 15. The upper trace data 120 shown in FIG. 15 were collected at 25 kV excitation voltage. The average intensity at each retraction distance is plotted, along with the calculated +/−3 $\sigma$ statistical error. The errors were obtained from the filter fit method used to extract the net peak counts. The data is compared to a data set without the GIO optic in place 122. Although no Ni was present in these no-optic spectra, they were fit for Ni, and the net Ni counts computed. The error bars are not shown, but would be about the same size as the error bars on the other trace, since the background level is the major contribution to the fitting process. Data in this figure show that the NiK$\alpha$ artifact peak is statistically not present beyond about 4 mm retraction from the optimal focus distance.

The foregoing studies indicate that a GIO x-ray optic employed in combination with an EDS detector provides a significant enhancement of the low energy x-ray spectrum detected. Intensity gains in the range of 4 to 20 times are seen from fluorine to boron. Intensities from the GIO are repeatable when proper care is used in positioning the EDS detector/GIO combination. The GIO can also provide a modest focusing effect by limiting the field of view seen by the EDS detector. A single spectral artifact peak was observed, which is small, and can easily be avoided.

Thus, a GIO optic in combination with an EDS detector may offer significant benefits for microanalysis performed at low excitation kV, where the reduction in intensities from the higher energy x-ray lines is not a factor. With some redesign, these types of GIO x-ray optics can be made smaller (at the expense of gain), allowing smaller detector-to-specimen distance and increased focusing effect.

Although the experiments performed employed a grazing incidence x-ray optic in combination with an EDS detector, it should be understood that any type of conventional x-ray optic may be used in combination with an EDS detector to improve EDS detection performance in accordance with the present invention. For example, a polycapillary x-ray optic, or a combined hybrid grazing incidence-type optic nested with a suitably sized polycapillary optic may be employed in combination with an EDS detector. (A hybrid grazing incidence/polycapillary optic is described in U.S. Pat. No. 5,926,522, incorporated herein by reference.)

Although the experiments described in detail herein were performed using a conventional SEM, it should be understood that the combined x-ray optic and EDS detector of the present invention may be employed most effectively in spectroscopy applications employing broad beam excitation, such as ESEM and x-ray fluorescence. In ESEM, the specimen is analyzed in a relatively high ambient pressure, contrasted to normal SEMs operating under high vacuum. Under these conditions, the incident electron beam can spread appreciably, such that the excited area of the specimen becomes large, reducing the spatial resolution of the EDS spectrometer. X-ray optics are useful in this application to spatially limit the x-rays of interest to those within the acceptance angle of the optic.

In this application, collimating grazing incidence or polycapillary optics, or a double focus polycapillary optic, would be preferred due to the critical focusing requirements of such optics. These types of optics require the x-rays to originate from a point source to be transmitted efficiently through the optic. As described previously, the grazing incidence optic described herein is not a true collimating optic, but it still shows a spatial filtering effect, as the point source of x-rays (beam position) is moved away from the central axis of the optic (see FIG. 11). This effect would be more pronounced for collimating or double-focus type x-ray optics.

It should be understood that the present invention is not limited to the particular exemplary embodiments and applications illustrated and described herein, but includes all such modified forms thereof must come within the scope of the following claims.

What is claimed is:

1. An x-ray detector, comprising
   (a) an energy dispersive spectroscopy detector; and
   (b) an x-ray optic mounted with respect to the energy dispersive spectroscopy detector to spatially limit the field of view of the energy dispersive spectroscopy detector to x-rays entering the x-ray optic and to direct the x-rays onto the energy dispersive spectroscopy detector with an optic gain greater than one for a range of x-ray energies below 1 keV.

2. The x-ray detector of claim 1 wherein the x-ray optic is mounted to the energy dispersive spectroscopy detector via a mounting assembly.

3. The x-ray detector of claim 1 wherein the x-ray optic is a grazing incidence x-ray optic.

4. The x-ray detector of claim 3 comprising additionally carbon applied to an outside surface of the grazing incidence x-ray optic at a tip of the grazing incidence x-ray optic where the x-rays enter the grazing incidence x-ray optic.

5. The x-ray detector of claim 1 comprising additionally a microscope including an energy source for directing a broad beam of energy unto a sample to produce x-rays therefrom, and wherein the energy dispersive spectroscopy detector and the x-ray optic are mounted in the microscope such that the x-ray optic spatially limits the field of view of the energy dispersive spectroscopy detector to x-rays produced from the sample that are directed by the x-ray optic onto the energy dispersive spectroscopy detector.

6. The x-ray detector of claim 5 wherein the microscope is an environmental scanning electron microscope and the energy source directs a beam of electrons toward a sample which becomes a broad beam where the beam contacts the sample.

7. A method for detecting x-rays from a sample, comprising the steps of:
   (a) providing an energy dispersive spectroscopy detector near the sample;
   (b) directing a beam of energy onto the sample to produce x-rays therefrom; and
   (c) directing the x-rays produced from the sample through an x-ray optic onto the energy dispersive spectroscopy detector such that the x-ray optic spatially limits the field of view of the energy dispersive spectroscopy detector to x-rays within an acceptance angle of the optic and with an optic gain greater than one for a range of x-ray energies below 1 keV.

8. The method of claim 7 wherein the x-ray optic is a grazing incidence x-ray optic.

9. The method of claim 8 comprising additionally the step of applying carbon to an outside surface of the grazing incidence x-ray optic at a tip of the grazing incidence x-ray optic where the x-rays enter the grazing incidence x-ray optic.

10. The method of claim 7 wherein the step of directing the x-rays produced from the sample through the x-ray optic includes the step of mounting the x-ray optic to the energy dispersive spectroscopy detector via a mounting assembly.

11. The method of claim 7 wherein the step of directing a beam of energy onto the sample includes directing an electron beam onto the sample in an environmental scanning electron microscope so that a broad electron beam is directed onto the sample.

* * * * *